United States Patent
Reddy

(10) Patent No.: US 7,865,249 B2
(45) Date of Patent: Jan. 4, 2011

(54) MEANS TO SECURELY FIXATE PACING LEADS AND/OR SENSORS IN VESSELS

(75) Inventor: G. Shantanu Reddy, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 606 days.

(21) Appl. No.: 11/534,558

(22) Filed: Sep. 22, 2006

(65) Prior Publication Data

US 2008/0077220 A1    Mar. 27, 2008

(51) Int. Cl.
*A61N 1/05* (2006.01)

(52) U.S. Cl. ...................................... 607/126

(58) Field of Classification Search ................ 607/126, 607/130, 131; 600/381
See application file for complete search history.

(56) References Cited

U.S. PATENT DOCUMENTS

| | | | |
|---|---|---|---|
| 4,280,512 A | 7/1981 | Karr et al. | |
| 4,913,164 A | 4/1990 | Greene et al. | |
| 5,071,407 A | 12/1991 | Termin et al. | |
| 5,170,802 A * | 12/1992 | Mehra | 607/126 |
| 5,179,962 A | 1/1993 | Dutcher et al. | |
| 5,221,261 A | 6/1993 | Termin et al. | |
| 5,224,491 A | 7/1993 | Mehra | |
| 5,238,007 A | 8/1993 | Giele et al. | |
| 5,344,439 A | 9/1994 | Otten | |
| 5,449,372 A | 9/1995 | Schmaltz et al. | |
| 5,514,174 A | 5/1996 | Heil, Jr. et al. | |
| 5,531,779 A | 7/1996 | Dahl et al. | |
| 5,645,580 A | 7/1997 | Moaddeb et al. | |
| 5,649,906 A | 7/1997 | Gory et al. | |
| 5,683,445 A | 11/1997 | Swoyer | |
| 5,843,163 A * | 12/1998 | Wall | 623/1.15 |
| 5,902,331 A | 5/1999 | Bonner et al. | |

(Continued)

FOREIGN PATENT DOCUMENTS

WO    2005053784 A2    6/2005

OTHER PUBLICATIONS

DeCock et al., "Repetitive intraoperative dislocation during transvenous left ventricular lead implantation," PACE 2004, 27:1589-1593.

(Continued)

*Primary Examiner*—Kennedy J Schaetzle
(74) *Attorney, Agent, or Firm*—Faegre & Benson LLP

(57) ABSTRACT

According to embodiments of the present invention, a cardiac lead system adapted for fixation to a vessel including an expandable fixation mechanism adapted to engage an inner surface of the vessel and a lead member comprising an anchor structure at distal end, the anchor structure configured to removably engage with fixation mechanism. Such anchor structure may be helical, and may removably engage fixation mechanism upon rotation or an application of torque, and may be extendable and/or retractable. Fixation mechanism may be polymer coated weave and/or mesh to trap anchor structure. Lead member and/or fixation mechanism may include electrodes and/or sensors, and lead member may include L-shape, S-shape, spiral, and/or sinusoidal shape for positioning of electrodes and/or sensors or for facilitated engagement of anchor structure. A guide wire attached to fixation mechanism during deployment may, prior to detachment, serve to guide lead member to a target site at fixation mechanism.

25 Claims, 11 Drawing Sheets

U.S. PATENT DOCUMENTS

| | | | |
|---|---|---|---|
| 5,954,761 A | 9/1999 | Machek et al. | |
| 5,964,795 A | 10/1999 | McVenes et al. | |
| 6,129,752 A * | 10/2000 | Neubauer et al. | 607/127 |
| 6,136,021 A | 10/2000 | Tockman et al. | |
| 6,161,029 A | 12/2000 | Spreigl et al. | |
| 6,397,109 B1 | 5/2002 | Cammilli et al. | |
| 6,445,958 B1 | 9/2002 | Machek et al. | |
| 6,510,347 B2 | 1/2003 | Borkan | |
| 6,697,676 B2 | 2/2004 | Dahl et al. | |
| 6,709,415 B2 | 3/2004 | Navia et al. | |
| 6,711,443 B2 | 3/2004 | Osypka | |
| 6,716,238 B2 | 4/2004 | Elliott | |
| 6,738,674 B2 | 5/2004 | Osypka | |
| 6,745,079 B2 | 6/2004 | King | |
| 6,824,562 B2 | 11/2004 | Mathis et al. | |
| 6,842,648 B2 | 1/2005 | Partridge et al. | |
| 6,882,887 B1 | 4/2005 | Shelchuk et al. | |
| 6,976,987 B2 | 12/2005 | Flores | |
| 7,082,336 B2 * | 7/2006 | Ransbury et al. | 607/126 |
| 7,306,598 B2 * | 12/2007 | Truckai et al. | 606/49 |
| 2001/0004683 A1 | 6/2001 | Gambale et al. | |
| 2002/0026228 A1 | 2/2002 | Schauerte | |
| 2002/0147484 A1 * | 10/2002 | Dahl et al. | 607/116 |
| 2002/0147487 A1 | 10/2002 | Sundquist et al. | |
| 2002/0161423 A1 | 10/2002 | Lokhoff et al. | |
| 2003/0023295 A1 | 1/2003 | Osypka | |
| 2003/0181966 A1 | 9/2003 | Morgan | |
| 2003/0199961 A1 | 10/2003 | Bjorklund et al. | |
| 2003/0204231 A1 | 10/2003 | Hine et al. | |
| 2004/0059404 A1 | 3/2004 | Bjorklund et al. | |
| 2004/0097965 A1 | 5/2004 | Gardeski et al. | |
| 2004/0249431 A1 * | 12/2004 | Ransbury et al. | 607/126 |
| 2005/0033394 A1 | 2/2005 | Seifert et al. | |
| 2005/0033395 A1 | 2/2005 | Seifert et al. | |
| 2005/0043765 A1 * | 2/2005 | Williams et al. | 607/9 |
| 2005/0070981 A1 | 3/2005 | Verma | |
| 2005/0080472 A1 * | 4/2005 | Atkinson et al. | 607/126 |
| 2005/0096718 A1 | 5/2005 | Gerber et al. | |
| 2005/0228471 A1 * | 10/2005 | Williams et al. | 607/126 |
| 2006/0106445 A1 | 5/2006 | Woollett | |
| 2006/0217779 A1 * | 9/2006 | Ransbury et al. | 607/36 |
| 2006/0224225 A1 * | 10/2006 | Ransbury et al. | 607/122 |
| 2006/0241736 A1 | 10/2006 | Haldeman | |
| 2006/0241737 A1 * | 10/2006 | Tockman et al. | 607/126 |
| 2006/0265021 A1 | 11/2006 | Herbert et al. | 607/40 |
| 2007/0043414 A1 * | 2/2007 | Fifer et al. | 607/126 |
| 2007/0066998 A1 | 3/2007 | Hansen et al. | |
| 2007/0208252 A1 * | 9/2007 | Makower | 600/424 |
| 2007/0255368 A1 * | 11/2007 | Bonde et al. | 607/116 |
| 2007/0282414 A1 * | 12/2007 | Soltis et al. | 607/122 |
| 2008/0065185 A1 * | 3/2008 | Worley | 607/119 |
| 2008/0077219 A1 * | 3/2008 | Williams et al. | 607/126 |
| 2008/0312712 A1 * | 12/2008 | Penner | 607/40 |

OTHER PUBLICATIONS

File History of U.S. Appl. No. 10/136,777 filed Apr. 30, 2002, entitled "Method and Apparatus for placing a Coronary Sinus/Cardiac Vein Pacing and Defibrillation Lead with Adjustable Electrode Spacing".
International Search Report and Written Opinion for Application No. PCT/US2008/059431, mailed Jul. 8, 2008.

\* cited by examiner

US 7,865,249 B2

MEANS TO SECURELY FIXATE PACING LEADS AND/OR SENSORS IN VESSELS

TECHNICAL FIELD

The present invention relates to implantable medical devices and, in particular, to fixation of cardiac leads and/or sensors in a patient's vascular system.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing. The lead typically consists of a flexible conductor, defining a central channel or lumen, surrounded by an insulating tube or sheath extending from an electrode at the distal end to a connector pin at the proximal end.

Cardiac lead placement may be accomplished by introducing the lead through a major blood vessel and advancing a distal end of the lead to a final destination in or near the heart. To facilitate cannulation of the vasculature, it is often helpful to first advance a guiding catheter through the desired vascular path. One difficulty with implanting leads in this fashion is that the cardiac lead has a tendency to become dislodged from its desired location during or after lead implantation. For example, when a clinician withdraws the guiding catheter, the lead may dislodge or otherwise reposition. Until tissue ingrowth ultimately fixes the lead at the desired site, cardiac leads may also become dislodged by subsequent physiological activity.

A variety of passive means devices have been secured to cardiac leads to affix the leads at a desired location in a patient's vasculature by exerting a radial force against vein walls. Nonetheless, there is a need in the art for a cardiac lead having a fixation mechanism which effectively affixes the cardiac lead at a desired position in a non-destructive manner, but which also allows the lead to be repositioned within or removed from the patient's vasculature, even after an extended implantation period.

SUMMARY

A cardiac lead system adapted for fixation to a vessel is provided, according to an embodiment of the present invention. The system includes an expandable fixation mechanism and a lead member. The expandable fixation mechanism includes an expanded position adapted to engage an inner surface of the vessel. The lead member has a proximal and distal ends. The distal end of the lead member includes an anchor structure, which is configured to removably engage the fixation mechanism.

The anchor structure may include a helical, corkscrew, barb, tine, and/or hook configuration. Anchor structures having a helical configuration may be configured to removably engage the fixation mechanism by rotating the anchor structure into the inner surface of the fixation mechanism. The fixation mechanism and/or the lead member may include one or more electrodes and/or one or more sensors. The expandable fixation mechanism may be coated with a polymer weave and/or polymer matrix to engage the anchor structure. The anchor structure may be retractable into and/or extendable from the lead member. Alternatively, the anchor structure may be fixed with respect to the lead member, and the anchor structure may be exposed by extending and retracting the lead member from within a guide catheter. Alternatively, the anchor structure may be fixed with respect to the lead member, and the anchor structure may be coated with a polyethylene glycol or mannitol for deployment.

A cardiac lead system adapted for fixation to a vessel is provided, according to another embodiment of the present invention. The system includes an expandable fixation mechanism and a lead member. The expandable fixation mechanism includes an expanded position adapted to engage an inner surface of the vessel. The lead member comprises a helix structure, which is configured to removably engage the fixation mechanism by rotation of the helix structure into the fixation mechanism.

A method for non-destructive anchoring of a cardiac lead member to a coronary vessel is provided, according to yet another embodiment of the present invention. A guide wire is passed into the coronary vessel, and a stent structure is deployed over the guide wire and into the coronary vessel. The stent structure is expanded to engage the inner surface of the coronary vessel. A lead member is deployed over the guide wire, the lead member including an anchor structure. According to some embodiments, the guide wire may be attached to the stent structure, and the lead member passed over the guide wire to a "landing zone" on the stent structure prior to removal of the guide wire from the stent structure. The anchor structure is then attached to the stent structure. The anchor structure may be helical, in which case attaching the anchor structure to the stent structure includes rotating the anchor structure into the stent structure. The anchor structure may also be extended and/or retracted, and may be removed from the stent structure according to embodiments of the present invention.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
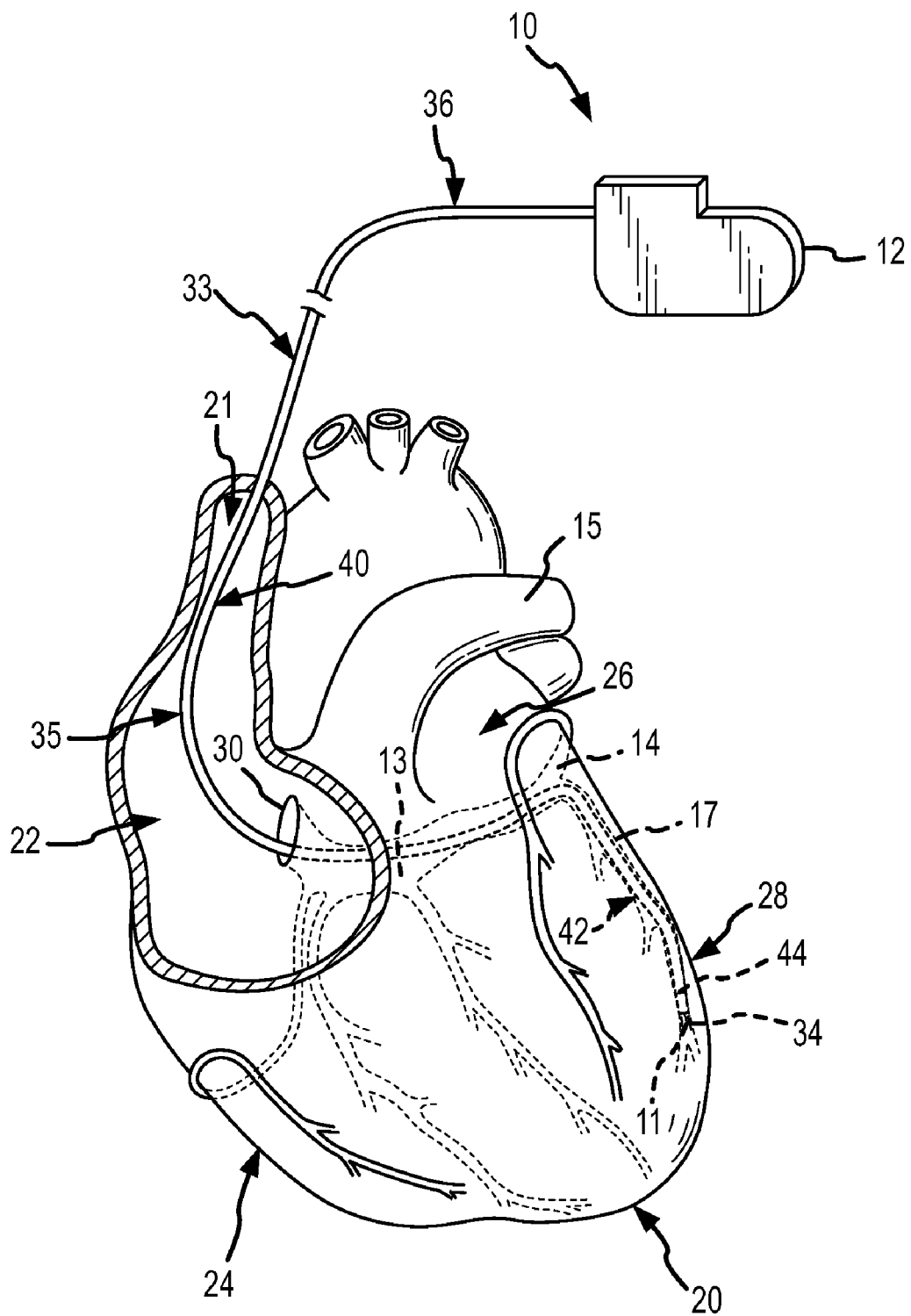
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a lead member 33 deployed in a patient's heart 20 from a superior vena cava 21. As is known in the art, the pulse generator 12 is typically implanted subcutaneously at an implantation location in the patient's chest or abdomen. As shown, the heart 20 includes a right atrium 22 and a right ventricle 24, a left atrium 26 and a left ventricle 28, a coronary sinus ostium 30 in the right atrium 22, a coronary sinus 13, and various cardiac branch vessels including a great cardiac vein 14 and an exemplary branch vessel 17.

As shown in FIG. 1, lead member 33 may include an elongate body 35 including a proximal region 36 and a distal region 40. The distal region 40 has a distal end 42 including an electrode 44 and terminating in an anchor structure 11, according to embodiments of the present invention. Anchor structure 11 may be removably engaged with a fixation mechanism 34 such as, for example, a stent structure.

To facilitate left ventricular pacing epicardially via a transveous approach, leads 33 may be deployed in coronary veins 17 through the coronary sinus 13. In some cases, instability of leads 33 may result in extended procedure times, re-operation, loss of capture, phrenic nerve stimulation, and loss of resynchronization therapy. Development of more stable leads 33 has generally involved shapes that enable the lead 33 or the tip of the lead 33 to push radially against the vessel 17 wall promoting anchoring. However, for such shaped leads, dislodgement and migration rates may remain high in some cases. For pacing and defibrillation lead members 33 placed in the right chambers of the heart 20, active fixation variants of leads have been used to penetrate the endocardium and myocardium to anchor the lead 33 in place. However, such actively fixated leads may result in infections or may become lodged within the tissue in a way that does not permit easy removal. Embodiments of the present invention provide an anchor structure 11 for secure and removable fixation to a fixation mechanism 34, without penetration of the vessel 17 wall.

Although FIG. 1 depicts lead member 33 deployed through branch vessel 17, lead member 33 may alternatively be deployed through and anchored within the pulmonary artery 15, according to some embodiments of the present invention. Furthermore, although FIG. 1 depicts lead member 33 as part of a cardiac rhythm management system 10 with an electrode 44, lead member 33 may alternatively include one or more sensors and/or one or more electrodes 44, and may couple the one or more sensors with a monitor instead of and/or in addition to pulse generator 12.

Figure 2:
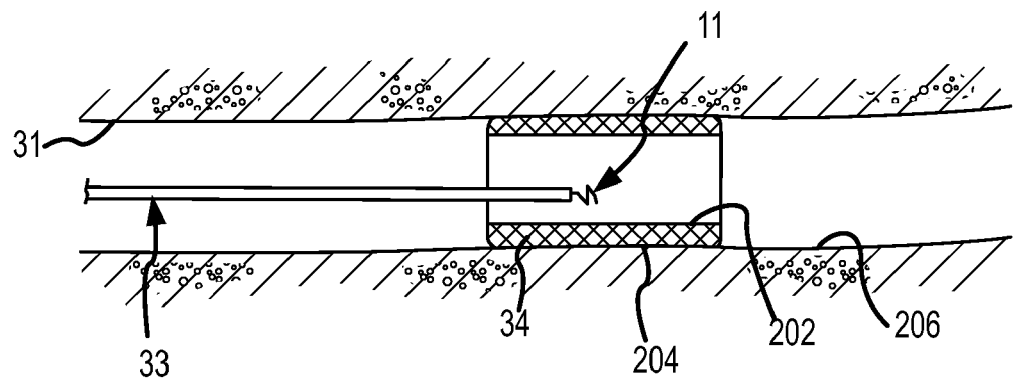
FIG. 2 depicts a partial cross sectional view of a blood vessel and fixation mechanism with a side elevation view of a lead member and anchor structure, according to embodiments of the present invention.
Figure 3:
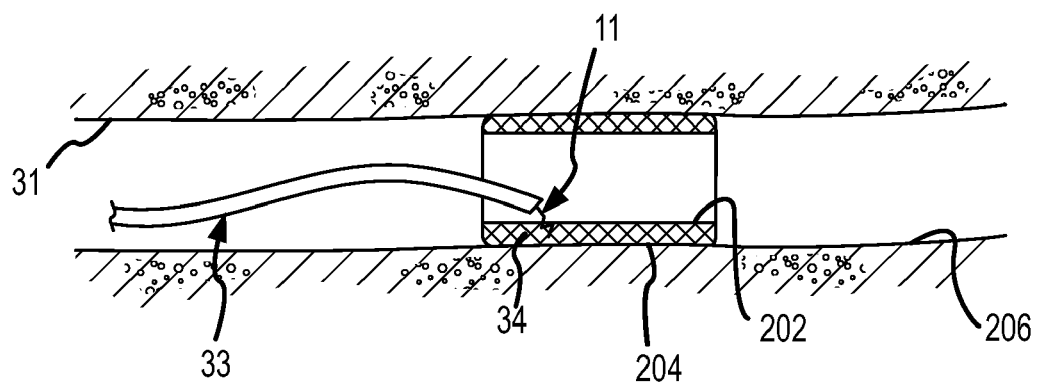
FIG. 3 depicts a partial cross sectional view of a blood vessel and fixation mechanism and a side elevation view of a lead member attached to the fixation mechanism via an anchor structure, according to embodiments of the present invention.

FIGS. 2-3 illustrate attachment of anchor structure 11 of lead member 33 to fixation mechanism 34 according to embodiments of the present invention. Fixation mechanism 34 may be deployed within a vessel 31 such as, for example, branch vessel 17 or pulmonary artery 15. Fixation mechanism 34 includes an inner surface 202 and an outer surface 204, and may be expandable according to some embodiments of the present invention. FIGS. 2-3 depict fixation mechanism 34 in an expanded position in which outer surface 204 of fixation mechanism 34 engages an inner surface 206 of vessel 31. According to some embodiments of the present invention, fixation mechanism 34 is a stent.

FIG. 3 depicts anchor structure 11 of lead member 33 removably engaged with inner surface 202 of fixation mechanism 34. Anchor structure 11 may be removably engaged with fixation mechanism 34 by turning, rotating, pushing, and/or hooking anchor structure 11 into inner surface 202, according to some embodiments of the present invention. As used herein, the term "removably engaged" is used in its broadest sense to refer to an engagement or coupling of two elements which may be reversed. Removably engaging anchor structure 11 with fixation mechanism 34 substantially deters detachment and/or drifting of anchor structure 11 and thus lead member 33 with respect to fixation mechanism 34, while permitting anchor structure 11 to be disengaged from fixation mechanism 34 through a reverse application of the turning, rotating, pushing, and/or hooking force, according to some embodiments of the present invention. Anchor structure 11 may engage the fixation mechanism 34 thereby actively fixating anchor structure 11 (and thus lead member 33) to fixation mechanism 34 but not penetrating the vessel 31 wall.

Anchor structure 11 is shown having a helical configuration in FIGS. 2-3. As such, anchor structure 11 may be removably engaged with inner surface 202 of fixation mechanism 34 by rotating and/or turning the anchor structure 11 into inner surface 202. According to some embodiments of the present invention, anchor structure 11 may be removably engaged with fixation mechanism 34 in a fashion similar to the way in which a wine bottle corkscrew may be removably engaged with a cork.

Figure 4:
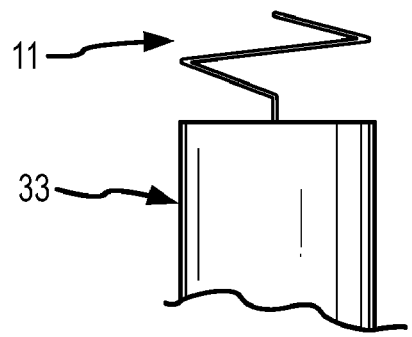
FIG. 4 illustrates a possible configuration of an anchor structure, according to embodiments of the present invention.
Figure 5:
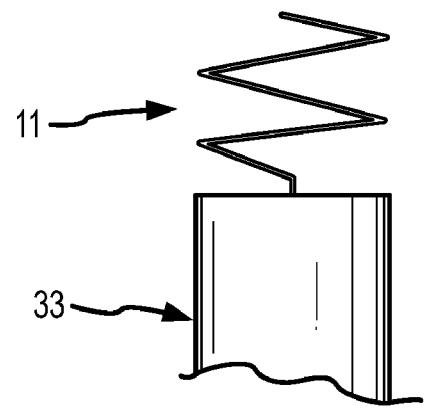
FIG. 5 illustrates a possible configuration of an anchor structure, according to embodiments of the present invention.
Figure 6:
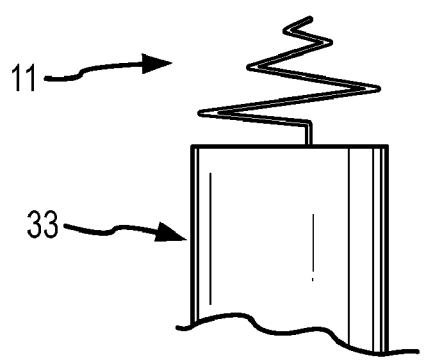
FIG. 6 illustrates a possible configuration of an anchor structure, according to embodiments of the present invention.
Figure 7:
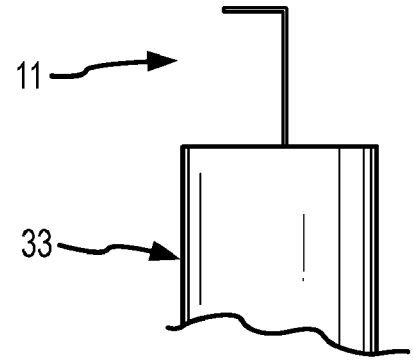
FIG. 7 illustrates a possible configuration of an anchor structure, according to embodiments of the present invention.
Figure 8:
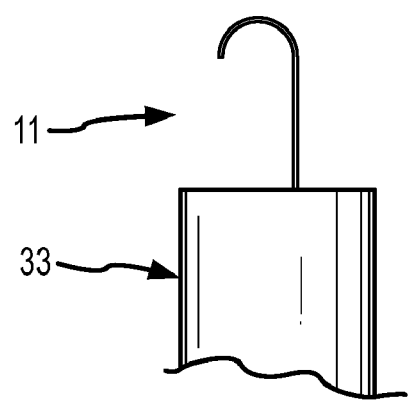
FIG. 8 illustrates a possible configuration of an anchor structure, according to embodiments of the present invention.
Figure 9:
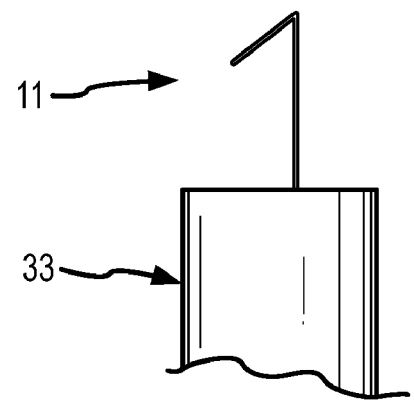
FIG. 9 illustrates a possible configuration of an anchor structure, according to embodiments of the present invention.

FIGS. 4-9 illustrate various alternative embodiments of anchor structure 11. FIGS. 4 and 5 illustrate side views of lead member 33 with an anchor structure 11 having a helical configuration; the helix of FIG. 4 is a single-coil helix, and the helix of FIG. 5 is a double-coil helix. FIG. 6 illustrates a side view of lead member 33 with an anchor structure 11 having a corkscrew configuration. According to some embodiments of the present invention, anchor structure 11 is a very short helix with a single turn, extending approximately one millimeter or less from lead member 33, and with a rounded end. FIGS. 7-9 depict side views of lead member 33 with an anchor structure 11 having tine, hook, and barb configurations, respectively. Although anchor structure 11 may have various configurations, a helical configuration may permit simple fixation and removal through application of torque. Based on the disclosure provided herein, one of ordinary skill in the art will recognize that various alternative configurations of anchor structure 11 may be utilized to achieve results similar to those achievable with the configurations of FIGS. 4-9; for example, the helical configurations of FIGS. 4-5 may be arranged for engagement with either clockwise or counterclockwise rotation of anchor structure 11 into fixation mechanism 34.

Figure 10:
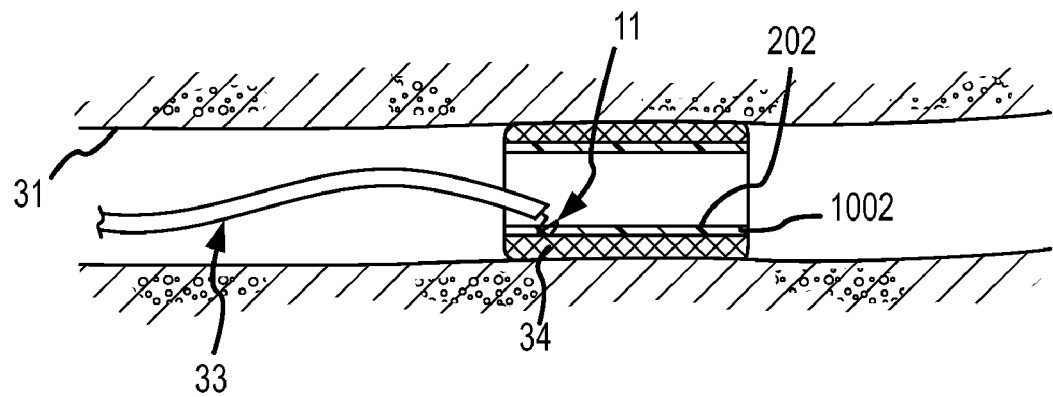
FIG. 10 depicts a partial cross sectional view of a blood vessel and fixation mechanism having a polymer coating and a side elevation view of a lead member attached to the fixation mechanism via an anchor structure, according to embodiments of the present invention.

FIG. 10 illustrates a fixation mechanism 34 having a polymer coating 1002 for inner layer 202, according to embodiments of the present invention. Anchor structure 11 may removably engage with fixation mechanism 34 by being driven into polymer coating 1002 such as, for example, through the application of torque or other turning force. According to some embodiments of the present invention, polymer layer 1002 is a DACRON® or expanded polytetrafluoroethylene (ePTFE) weave or polymer matrix. Anchor structure 11 may engage the polymer layer 1002 thereby actively fixating anchor structure 11 (and thus lead member 33) to fixation mechanism 34 but not penetrating the vessel 31 wall.

Figure 11:
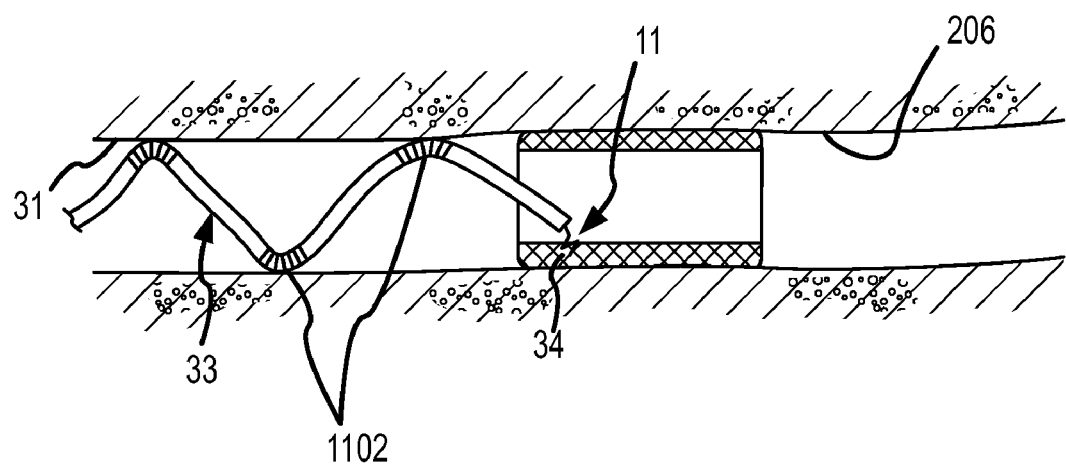
FIG. 11 depicts a partial cross sectional view of a blood vessel and fixation mechanism and a side elevation view of a lead member having multiple electrodes and attached to the fixation mechanism via an anchor structure, according to embodiments of the present invention.

FIG. 11 depicts a lead member 33 having multiple electrodes 1102 spaced at intervals along lead member 33, according to embodiments of the present invention. Lead member 33 may have a sinusoidal, spiral, or other non-linear shape, as depicted, to permit electrodes 1102 to contact the inner surface 206 of vessel 31 when anchor structure 11 is engaged with fixation mechanism 34. According to some embodiments of the present invention, lead member 33 is initially substantially straight and then assumes the depicted sinusoidal, spiral, or other non-linear shape upon removal of a stylet and/or guide wire from lead member 33.

Figure 12:
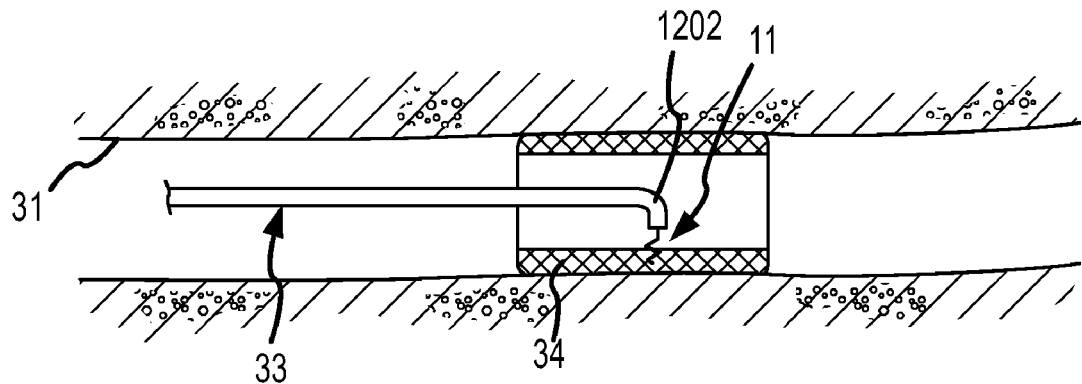
FIG. 12 depicts a partial cross sectional view of a blood vessel and fixation mechanism and a side elevation view of an L-shaped lead member attached to the fixation mechanism via an anchor structure, according to embodiments of the present invention.

FIG. 12 illustrates a lead member 33 having a bend 1202 which creates an L-shape lead member 33 according to embodiments of the present invention. Such an L-shape configuration permits anchor structure 11 to protrude at an angle from the longitudinal axis of lead member 33 (instead of in-line with lead member 33) which, in turn, may facilitate engagement of anchor structure 11 with fixation mechanism 34. According to some embodiments of the present invention, lead member 33 is initially substantially straight and then assumes the depicted L-shape upon removal of a stylet and/or guide wire from lead member 33.

Figure 13:
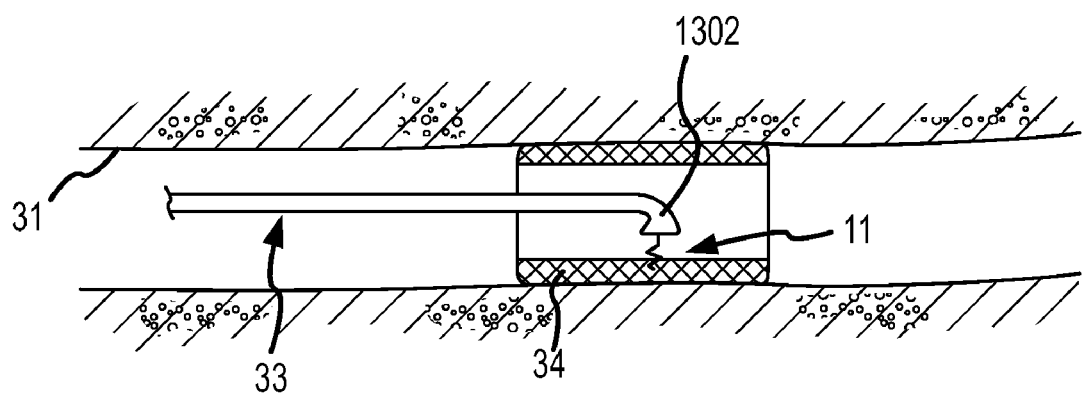
FIG. 13 depicts a partial cross sectional view of a blood vessel and fixation mechanism and a side elevation view of another L-shaped lead member attached to the fixation mechanism via an anchor structure, according to embodiments of the present invention.

In a similar fashion, FIG. 13 illustrates a lead member 33 having a head portion 1302 which permits anchor structure 11 to protrude at an angle from the longitudinal axis of lead member 33. Anchor structure 11 may protrude at a substantially right angle from the longitudinal axis of lead member 33, for example. According to some embodiments of the present invention, head portion 1302 may be shaped with rounded edges to facilitate deployment of lead member 33 through vessel 31. According to some embodiments, anchor structure 11 is fixed and may be coated with a dissolvable substance to prevent anchor structure 11 from catching or damaging a patient's vasculature during deployment of lead member 33.

Figure 14:
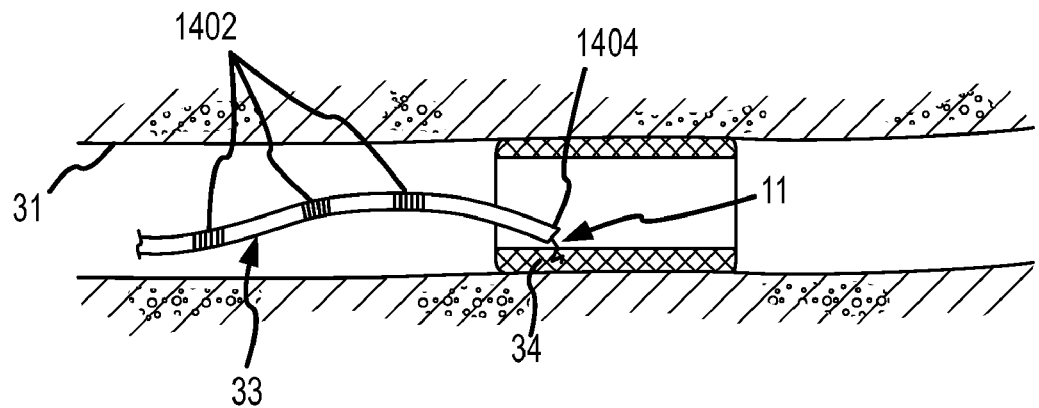
FIG. 14 depicts a partial cross sectional view of a blood vessel and fixation mechanism and a side elevation view of a lead member having multiple electrodes and attached to the fixation mechanism via an anchor structure, according to embodiments of the present invention.
Figure 15:
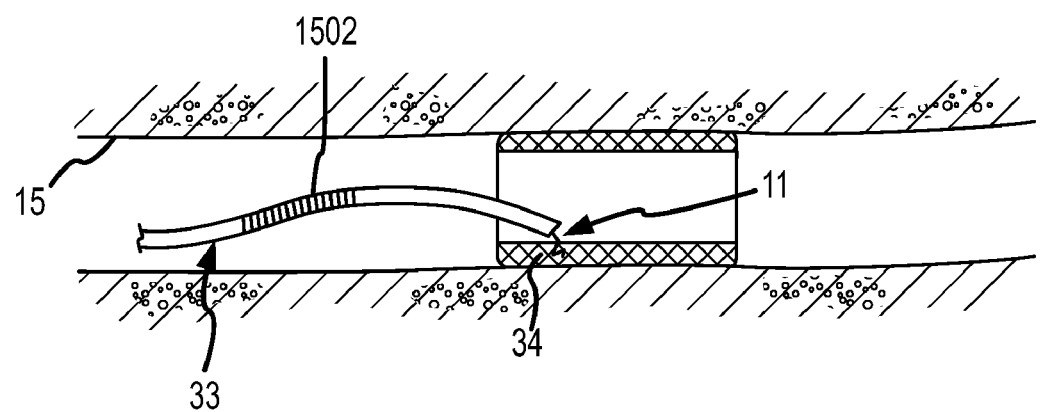
FIG. 15 depicts a partial cross sectional view of a pulmonary artery and fixation mechanism and a side elevation view of a lead member having a sensor and attached to the fixation mechanism via an anchor structure, according to embodiments of the present invention.

FIGS. 14 and 15 depict various alternative uses of a lead member 33 anchored to a fixation mechanism 34 according to embodiments of the present invention. FIG. 14 depicts a lead member 33 having multiple electrodes 1402 spaced at intervals along lead member 33. Use of multiple lead member 33/fixation mechanism 34 combinations in heart 20 may permit a series of electrodes to be available to optimize synchronization and mitigate issues such as high pacing thresholds and diaphragmatic stimulation. According to some embodiments of the present invention, anchor structure 11 and distal tip 1404 of lead member 33 are electrically inactive and/or insulated and provide anchoring and/or fixation for lead member 33. According to other embodiments, anchor structure 11 and/or distal tip 1404 are electrically active and are configured to energize a metallic and/or conductive fixation mechanism 34 which, in turn, may operate electrodes and/or sensors contained on and/or within fixation mechanism 34.

FIG. 15 depicts a lead member 33 having a pressure sensor module 1502 and deployed in the pulmonary artery 15. According to some embodiments of the present invention, fixation mechanism 34 permits adequate blood flow through pulmonary artery 15 after deployment. Pressure sensor 1502 may be used to evaluate decompensation, for example. Attaching lead member 33 to fixation mechanism 34 in pulmonary artery 15 permits placement of sensors within lead member 33 and/or fixation mechanism 34 without injuring or damaging the relatively fragile pulmonary artery 15, according to embodiments of the present invention.

Figure 16:
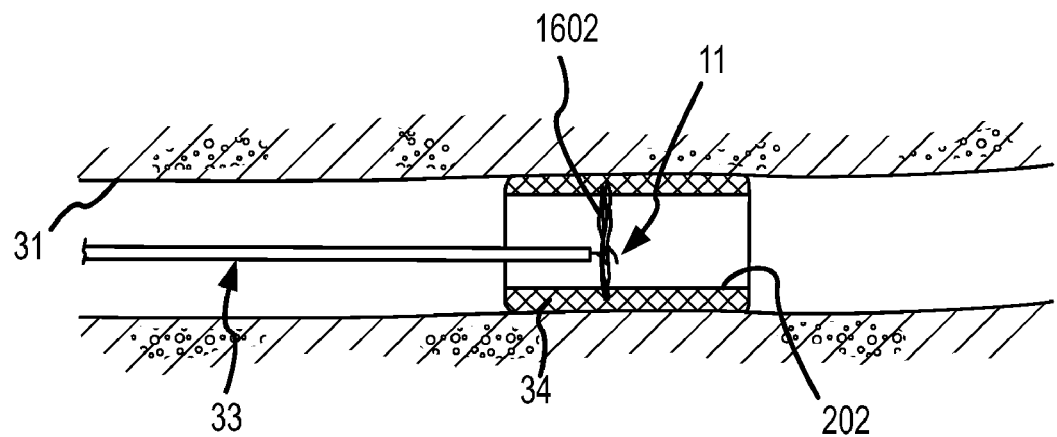
FIG. 16 depicts a partial cross sectional view of a blood vessel and fixation mechanism having a net and a side elevation view of a lead member attached to the net via an anchor structure, according to embodiments of the present invention.

FIG. 16 illustrates a lead member 33 with an anchor structure 11 removably engaged with a net 1602. Net 1602 connects at least two points along inner surface 202 of fixation mechanism 34. According to some embodiments of the present invention, net 1602 is a polymer layer of a DACRON® or expanded polytetrafluoroethylene (ePTFE) weave or polymer matrix deployed in a net-like fashion across the diameter of inner surface 202. According to some embodiments of the present invention, a pore size of net 1602 is optimized to enable blood flow, although net 1602 may also include multiple layers to trap and fixate anchor structure 11 whether anchor structure 11 includes the helix configuration of FIGS. 4-5, the corkscrew configuration of FIG. 6, or the barb/tine/hook configurations of FIGS. 7-9. Net 1602 may also include a metallic and/or conductive structure, such as interlaced metal wires, to provide energization of a metallic and/or conductive fixation mechanism 34 which, in turn, may operate electrodes and/or sensors contained on and/or within fixation mechanism 34.

Figure 17:
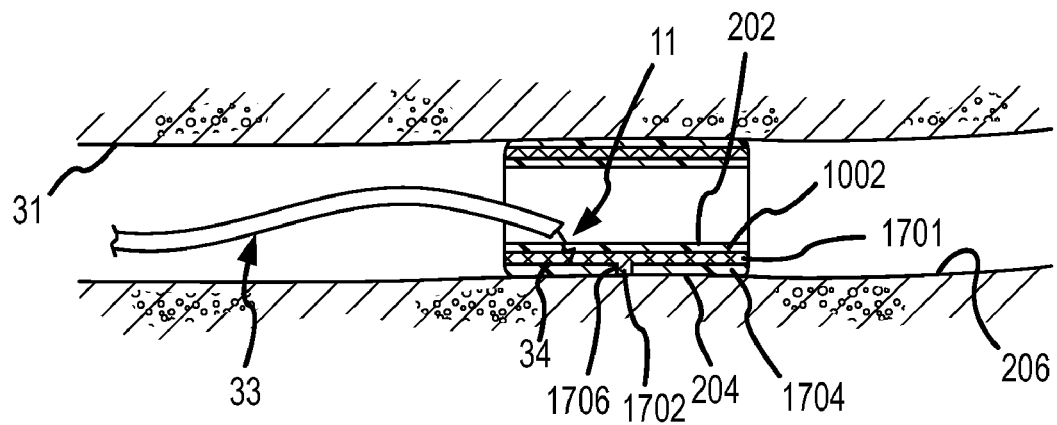
FIG. 17 depicts a partial cross sectional view of a blood vessel and fixation mechanism having an electrode and inner and outer polymer layers and a side elevation view of a lead member attached to the fixation mechanism via an anchor structure, according to embodiments of the present invention.

FIG. 17 depicts a fixation mechanism 34 having a first polymer coating 1002 for inner layer 202 and a second polymer coating 1704 for outer layer 204 of fixation mechanism 34. According to some embodiments of the present invention, polymer layers 1002 and/or 1704 are a DACRON® or expanded polytetrafluoroethylene (ePTFE) weave or polymer matrix. Outer surface 204 contacts inner surface 206 of vessel 31, and according to some embodiments, polymer layer 1704 acts as an electrical insulator between fixation mechanism 34 and inner surface 206 of vessel 31.

Fixation mechanism 34 includes a metallic and/or conductive layer 1701 between polymer layers 1002, 1704. According to some embodiments of the present invention, a gap 1706 formed in polymer layer 1704 permits a point electrode 1702 to protrude from metallic layer 1701 and against inner surface 206 of vessel 31. Anchor structure 11 may be electrically active to energize fixation mechanism 34, and thus may provide electrical impulses to vessel 31 via electrode 1702 when anchor structure 11 of lead member 33 is removably engaged with fixation mechanism 34. According to some embodiments of the present invention, polymer layer 1002 is insulative, and an electrically active anchor structure 11 penetrates polymer layer 1002 to engage with conductive layer 1701. Preferential orientation of electrodes 1702 could occur along the heart 20 wall.

Figure 18:
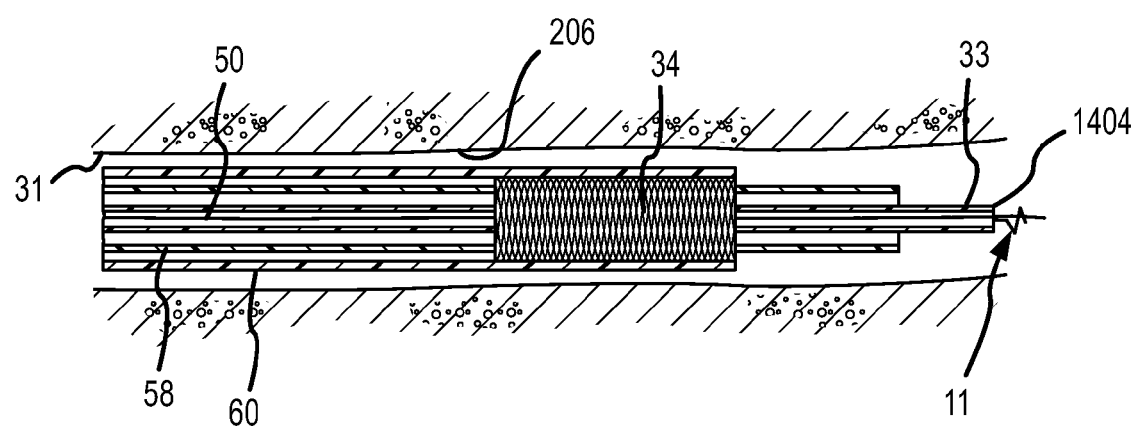
FIG. 18 depicts a partial cross sectional view of a blood vessel, illustrating a lead member within an inner guide catheter and a fixation mechanism between the inner guide catheter and the outer guide catheter, according to embodiments of the present invention.
Figure 19:
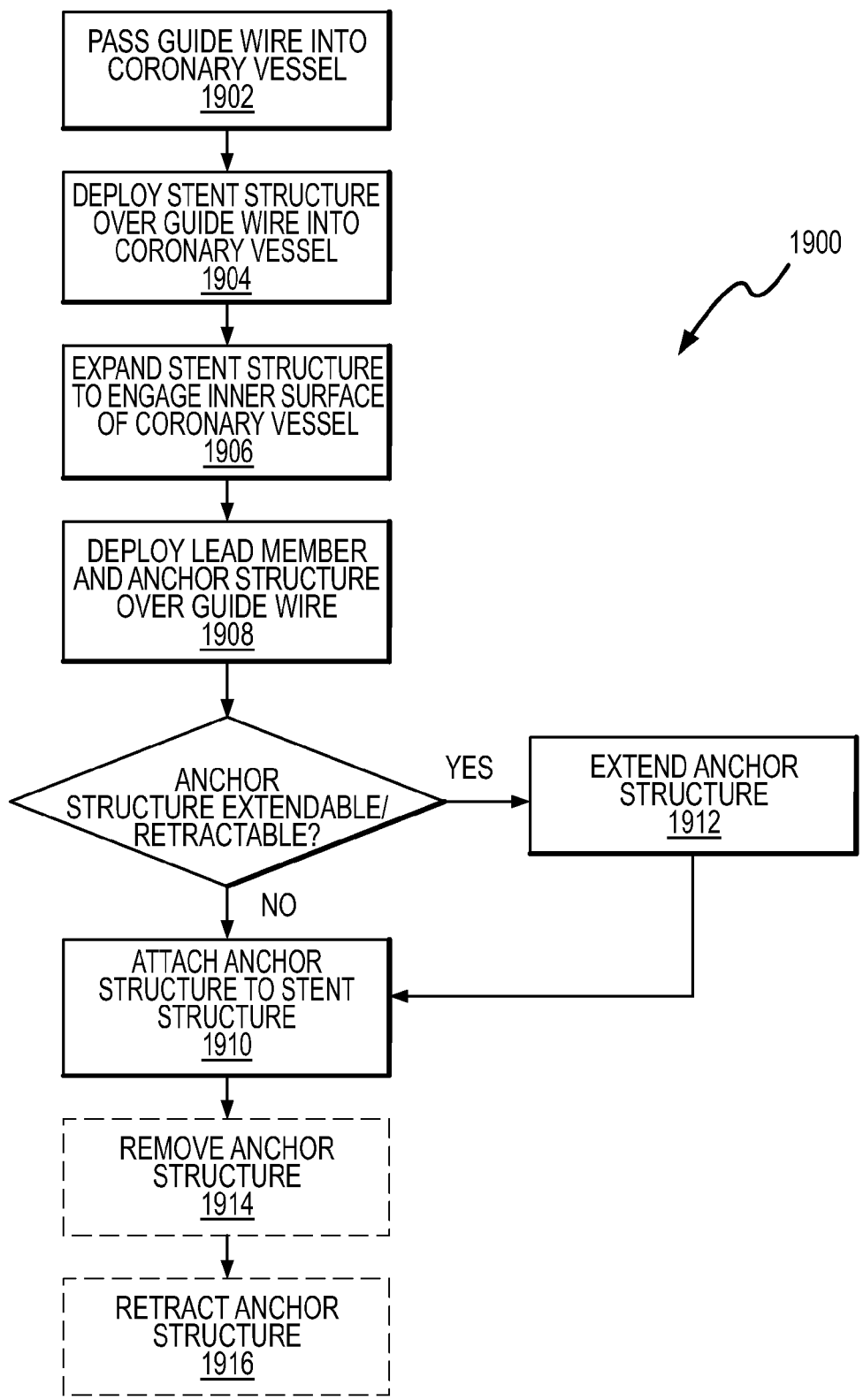
FIG. 19 depicts a flow chart illustrating a method for non-destructively anchoring a lead member to a coronary vessel.
Figure 20:
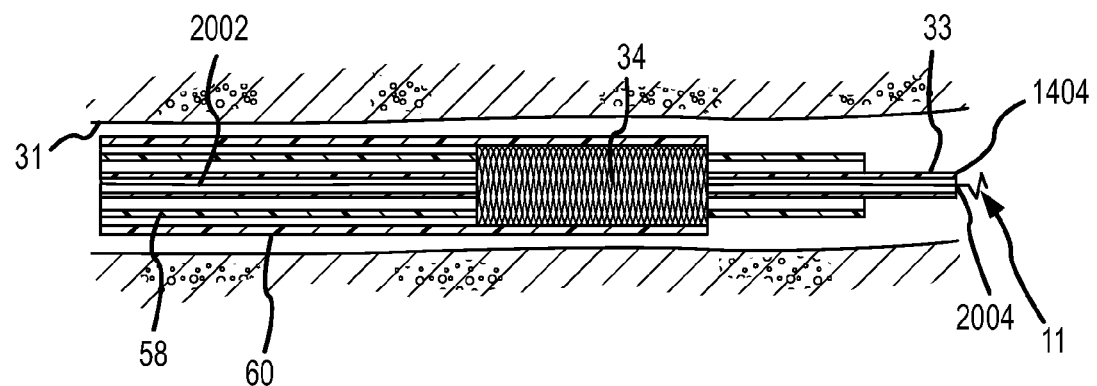
FIG. 20 depicts a partial cross sectional view of a blood vessel, illustrating a lead member within an inner guide catheter and a fixation mechanism between the inner guide catheter and the outer guide catheter, according to embodiments of the present invention.

FIGS. 18-20 illustrate a method for non-destructive anchoring of lead member 33 to coronary vessel 31 according to embodiments of the present invention. FIG. 19 depicts a flow chart 1900 showing a method of anchoring lead member 33 to vessel 31 according to one embodiment of the present invention. A guide wire 50 is passed through the patient's vasculature and into coronary vessel 31 (block 1902). Lead member 33 may be pre-loaded over an inner guide catheter 58 such that fixation mechanism 34 is in a compressed position between inner guide catheter 58 and outer guide catheter 60. Fixation mechanism 34, such as the stent structure depicted in FIG. 18, may then be deployed over guide wire 50 and into coronary vessel 31 (block 1904) by deploying the inner guide catheter 58 and outer guide catheter 60 over guide wire 50. Inner guide catheter 58 is then pushed in a distal direction with respect to outer guide catheter 60, or outer guide catheter 60 is then pulled in a proximal direction with respect to inner guide catheter 58, such that fixation mechanism 34 deploys to an expanded position (block 1906) shown in FIGS. 2-3 and 10-17, such that fixation mechanism 34 engages inner surface 206 of vessel 31.

Lead member 33 and anchor structure 11 may also be deployed over guide wire 50 (block 1908), either at the same time as fixation mechanism 34 or subsequent to deployment of fixation mechanism 34. According to some embodiments of the present invention, anchor structure 11 is extendable and/or retractable. If anchor structure 11 is extendable, anchor structure 11 may then be extended from lead member 33 and/or inner guide catheter 58 (block 1912). Anchor structure 11 may be attached to fixation mechanism 34 (block 1910); for example, a helical anchor structure 11 may be attached to fixation mechanism 34 by applying torque to anchor structure 11 to drive anchor structure 11 into fixation mechanism 34 as depicted in FIGS. 3 and 10-17. According to some embodiments of the present invention, deploying fixation mechanism 34 between outer guide catheter 60 and inner guide catheter 58 may serve to prevent premature snagging of anchor structure 11 on fixation mechanism 34.

Figure 21:
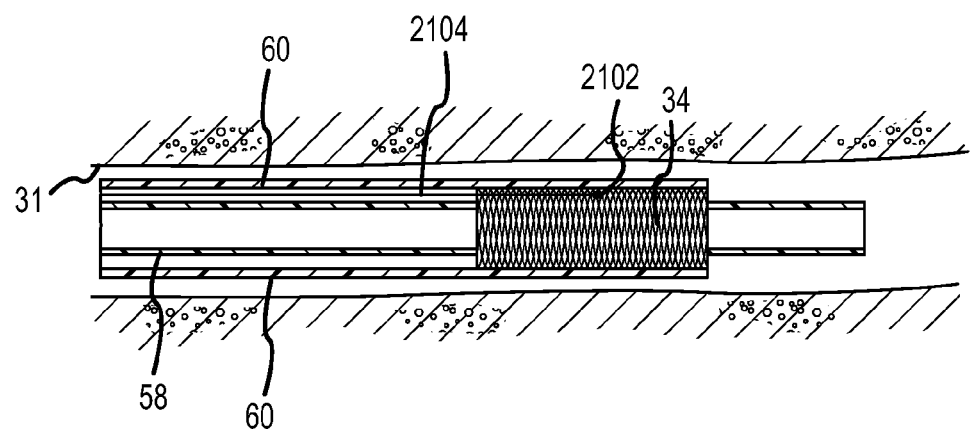
FIG. 21 depicts a partial cross sectional view of a blood vessel, illustrating a guide wire attached to a fixation mechanism between an inner guide catheter and an outer guide catheter.
Figure 22:
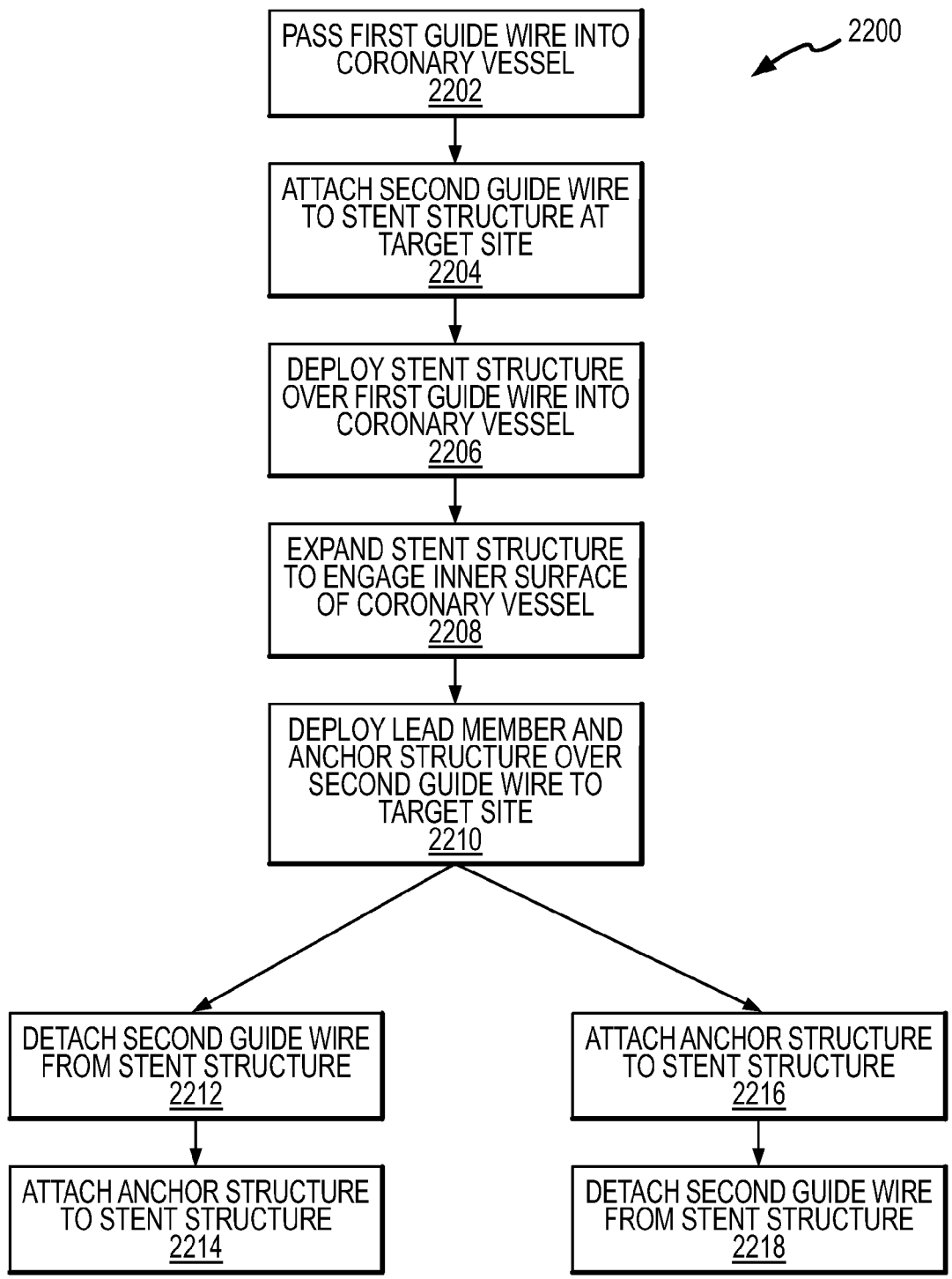
FIG. 22 depicts a flow chart illustrating a method for non-destructively anchoring a lead member to a coronary vessel.

FIGS. 21 and 22 illustrate an alternative method for non-destructive anchoring of lead member 33 to coronary vessel 31 according to embodiments of the present invention. FIG. 22 depicts a flow chart 2200 showing a method of anchoring lead member 33 to vessel 31 according to one embodiment of the present invention. A first guide wire may be passed into coronary vessel 31 (block 2202), and a second guide wire 2104 may be attached to a stent structure 34 at a target site 2102 (block 2204). According to some embodiments of the present invention, guide wire 2104 may be designed to be broken away or snapped off of fixation mechanism 34 subsequent to deployment of lead member 33. Stent structure 34 may be deployed over the first guide wire into coronary vessel 31 (block 2206), and expanded to engage an inner surface of coronary vessel 31 (block 2208). Such expansion may be achieved with a self-expanding stent structure 34 and/or with balloon expansion of stent structure 34, for example. Lead member 33, along with anchor structure 11, may be navigated over the second guide wire 2104 to the target site 2102 (block 2210). According to some embodiments of the present invention, the second guide wire 2104 is then detached from the stent structure 34 (block 2212) and the anchor structure 11 is attached to stent structure 34 (block 2214). Alternatively, anchor structure 11 may be attached to stent structure 34 (block 2216) prior to detachment of second guide wire 2104 from stent structure 34 (block 2218). According to some embodiments of the present invention, guide wire 2104 may be J-shaped near target site 2102 to prevent premature snagging of anchor structure 11 on fixation mechanism 34 prior to anchor structure 11 reaching the vicinity of target site 2102.

According to some embodiments of the present invention, anchor structure 11 is rigidly or semi-rigidly fixed on distal tip 1404, and torque is applied to anchor structure 11 by rotating lead member 33. For example, lead member 33 may be rotated within inner guide catheter 58, and inner guide catheter 58 may serve to help balance and position lead member 33 prior to and during rotation. Anchor structure 11 may be positioned in the vicinity of an inner surface 202 of fixation mechanism 34 and rotated and/or translated until an end of anchor structure 11 catches and penetrates fixation mechanism 34. According to such embodiments, extending anchor structure 11 includes extending lead member 33 from within inner guide catheter 58 to expose anchor structure 11. According to some embodiments of the present invention, an anchor structure 11 which is rigidly or semi-rigidly fixed on distal tip 1404 may be coated with a smooth dissolvable compound, such as a polyethylene glycol or mannitol, to facilitate deployment of lead member 33 through the patient's vasculature.

Anchor structure 11 is removable, according to embodiments of the present invention. Reasons for removal of lead member 33 and anchor structure 11 may include lack of response to a therapy, inadequate pressure reading, or infection associated with the wound site associated with pulse generator 12 or with the vascular access site, for example. In some cases, anchor structure 11 may be removed and re-anchored and/or re-implanted. In other cases, such as cases in which it is recommended that all links to the pulse generator 12 pocket area be removed, anchor structure 11 and lead member 33 may be completely removed from the patient. Anchor structure 11 may optionally be removed from fixation mechanism 34 (block 1914); for example, an anchor structure 11 having a helical configuration may be removed from fixation mechanism 34 by applying a torque to the anchor structure 11 opposite to the torque used to engage anchor structure 11 with fixation mechanism 34. Such a reverse turning, rotation, and/or application of torque may serve to "unscrew" and/or "unthread" anchor structure 11 from fixation mechanism 34. If anchor structure 11 is retractable, anchor structure 11 may be retracted (block 1916) for facilitated removal from the patient through the patient's vasculature. According to some embodiments of the present invention, fixation mechanism 34 is non-removable; however, fixation mechanism 34 may be made and used to feature no direct linkage via a lumen in the lead 33 or sensor between an infection site and fixation mechanism 34, such that abandoning fixation mechanism 34 may not be a concern.

According to embodiments of the present invention, guide wire 50 may be a stylet configured to substantially straighten lead member 33. A distal end of lead member 33 may be configured to assume an S-shape (as depicted in FIGS. 3, 10, 14, 15, 17), a sinusoidal or spiral shape (as depicted in FIG. 11), and/or an L-shape (as depicted in FIGS. 12-13) in the absence of a reinforcing stylet 50, for example. According to such embodiments, stylet 50 may be removed after engagement of anchor structure 11 with fixation mechanism 34 to permit lead member 33 to assume a desired configuration; alternatively, stylet 50 may be removed prior to engagement of anchor structure 11 with fixation mechanism 34 to achieve a desirable angle of anchor structure 11 with respect to fixation mechanism 34 to facilitate engagement of anchor structure 11 to fixation mechanism 34.

According to other embodiments of the present invention, anchor structure 11 is movable with respect to lead member 33. FIG. 20 depicts one such embodiment with a lead member 33 having a drive shaft 1902 coupled with anchor structure 11 through a hole 2004 in distal tip 1404. According to such embodiments, torque may be applied to anchor structure 11 by applying torque to drive shaft 2002, which moves substantially independently relative to lead member 33. According to some embodiments of the present invention, anchor structure 11 is retractable into lead member 33 by pulling and/or rotating drive shaft 2002 to bring anchor structure 11 into lead member 33 through hole 2004, and is extendable from lead member 33 by pushing and/or rotating drive shaft 2002 to bring anchor structure 11 out of lead member 33 through hole 2004. According to some embodiments of the present invention, anchor structure 11 maintains a substantially straight configuration when retracted within lead member 33 and assumes a configuration similar to a configuration depicted in FIGS. 4-9 when extended from lead member 33. Such a dynamic configuration may be achieved, for example, by imparting anchor structure 11 with a memory. According to alternative embodiments of the present invention, an extendable-retractable mechanism could be utilized which keeps anchor structure 11 (such a helical anchor structure 11) inside lead member 33 until exposure is desired by either rotating drive shaft 2002 or a stylet or by turning a terminal pin and activating a threaded or post-style advancement mechanism.

Drive shaft 2002 may also be flexible, to permit use of a drive shaft 2002 and anchor structure 11 combination with embodiments of lead member 33 such as those depicted in FIGS. 12 and 13. Drive shaft 2002 may simply bend at bend 1202 or at head 1302 to transform a torque about the longitudinal axis of lead member 33 to a torque about the longitudinal axis of anchor structure 11. Alternatively, head 1302 may, for example, include a type of universal joint to otherwise transform a torque about the longitudinal axis of lead member 33 to a torque about the axis of anchor structure 11.

Embodiments of the present invention utilize relatively straightforward implant techniques, feature positional stability, and offer ease of removal for lead members 33. Fixation mechanism 34 may be self-expanding or balloon deployable, according to embodiments of the present invention. Fixation mechanism 34 may also have very clear radiographic features to facilitate deployment, according to some embodiments. According to some embodiments of the present invention, fixation mechanism 34 is made with a nitinol, stainless steel, shape memory alloys, polymers, and/or cobalt chromium. According to some embodiments of the present invention, fixation mechanism 34 may be electrically active and may be made with or include a nickel or platinum alloy. According to some embodiments of the present invention, fixation mechanism 34 and/or outer layer 1704 may be made with a material, such as, for example, a mesh or porous material, which facilitates in-growth of tissue into fixation mechanism 34 and/or of fixation mechanism 34 into tissue; for example, fixation mechanism 34 may include a Gore®- or ePTFE-type material. According to some embodiments of the present invention, anchor structure 11 may be made with a metal, polymer, alloy, or other suitable material which gives anchor structure 11 enough strength and rigidity to puncture and/or engage with fixation mechanism 34 or with a fabric weave or mesh of fixation mechanism 34 and to retain engagement therewith until intentionally removed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A cardiac lead system adapted for fixation to a vessel, the system comprising:
    an expandable fixation mechanism having an expanded position adapted to engage an inner surface of the vessel; and
    a lead member having a proximal end and a distal end, the distal end comprising a helix structure,
    wherein the helix structure removably engages the fixation mechanism by rotation of the helix structure into the fixation mechanism.

2. The system of claim 1, wherein the helix structure comprises a single-coil configuration.

3. The system of claim 1, wherein the inner surface of the vessel is a first inner surface, wherein the fixation mechanism comprises:
    an outer surface adapted to engage the first inner surface;
    a second inner surface; and
    a net connecting at least two points along the second inner surface, and wherein the helix structure is configured to removably engage the fixation mechanism by rotation of the helix structure into the net.

4. The system of claim 1, wherein the inner surface of the vessel is a first inner surface, wherein the fixation mechanism comprises:
    an outer surface adapted to engage the first inner surface; and
    a second inner surface comprising a coating of polymer, and wherein the helix structure is configured to removably engage the fixation mechanism by rotation of the helix structure into the coating of polymer.

5. The system of claim 4, wherein the coating of polymer is a polymer weave structure.

6. The system of claim 4, wherein the coating of polymer is a polymer mesh structure.

7. The system of claim 4, wherein the coating of polymer is a first coating of polymer, the outer surface comprising a second coating of polymer.

8. The system of claim 7, wherein the helix structure is electrically active, wherein the second coating of polymer includes at least one gap, wherein the fixation mechanism further comprises at least one electrode configured to contact the first inner surface through the at least one gap, wherein the fixation mechanism comprises a metallic structure in contact with the at least one electrode, and wherein the helix structure is configured to removably engage the fixation mechanism by rotation of the helix structure into the metallic structure through the first coating of polymer.

9. The system of claim 4, wherein the polymer is selected from the group consisting of: DACRON®, expanded polytetrafluoroethylene, and Teflon®.

10. The system of claim 1, wherein the helix structure removably engages the fixation mechanism by rotation of the helix structure into the fixation mechanism without penetrating the inner surface of the vessel.

11. A cardiac lead system adapted for fixation to a vessel, the system comprising:
an expandable fixation mechanism having an expanded position adapted to engage an inner surface of the vessel; and
a lead member having a proximal end and a distal end, the distal end comprising an anchor structure,
wherein the anchor structure is substantially rigid and removably engages the fixation mechanism by penetrating the fixation mechanism.

12. The system of claim 11, wherein the fixation mechanism is a stent.

13. The system of claim 11, wherein the anchor structure comprises a helical configuration.

14. The system of claim 13, wherein the anchor structure protrudes longitudinally from the lead member, and wherein the anchor structure is configured to removably engage the fixation mechanism by rotating the anchor structure into the fixation mechanism.

15. The system of claim 11, wherein the anchor structure comprises a configuration selected from the group consisting of: a hook configuration, a tine configuration, a barb configuration, and a corkscrew configuration.

16. The system of claim 11, wherein the lead member comprises at least one electrode.

17. The system of claim 16, wherein the at least one electrode is a multiplicity of electrodes, and wherein each of the multiplicity of electrodes is spaced at an interval along the lead member.

18. The system of claim 17, wherein at least a portion of the lead member comprises a substantially sinusoidal shape to permit the multiplicity of electrodes to contact the inner surface of the vessel at different locations.

19. The system of claim 11, wherein the fixation mechanism is electrically conductive and comprises at least one electrode in contact with the inner surface, and wherein the anchor structure is electrically active.

20. The system of claim 11, wherein the anchor structure is extendable from within the lead member.

21. The system of claim 20, wherein the anchor structure is retractable back into the lead member.

22. A cardiac lead system adapted for fixation to a vessel, the system comprising:
an fixation mechanism having an inner surface, an outer surface, and an expanded position in which the outer surface of the fixation mechanism engages an inner surface of the vessel; and
a lead member having a proximal end and a distal end, the distal end comprising an anchor structure,
wherein the anchor structure removably engages the inner surface of the fixation mechanism by penetrating the fixation mechanism.

23. The system of claim 22, wherein the fixation mechanism is a stent.

24. The system of claim 22, wherein the anchor structure comprises a helical configuration.

25. The system of claim 22, wherein the anchor structure protrudes from the lead member, and wherein the anchor structure is configured to removably engage the fixation mechanism by rotating the anchor structure into the fixation mechanism.

* * * * *